United States Patent
Thakur et al.

(10) Patent No.: US 10,850,093 B2
(45) Date of Patent: Dec. 1, 2020

(54) LEAD INTEGRITY MONITORING

(71) Applicant: Cardiac Pacemakers, Inc., St. Paul, MN (US)

(72) Inventors: Pramodsingh H. Thakur, Woodbury, MN (US); Deepa Mahajan, Roseville, MN (US); Qi An, Blaine, MN (US); Keith R. Maile, New Brighton, MN (US); David J. Ternes, Roseville, MN (US); Zhe Shen, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 613 days.

(21) Appl. No.: 15/486,113

(22) Filed: Apr. 12, 2017

(65) Prior Publication Data

US 2017/0296810 A1 Oct. 19, 2017

Related U.S. Application Data

(60) Provisional application No. 62/322,137, filed on Apr. 13, 2016.

(51) Int. Cl.
*A61N 1/08* (2006.01)
*A61N 1/37* (2006.01)
*A61N 1/372* (2006.01)

(52) U.S. Cl.
CPC ............... *A61N 1/08* (2013.01); *A61N 1/37* (2013.01); *A61N 1/371* (2013.01);
(Continued)

(58) Field of Classification Search
CPC . A61N 1/08; A61N 1/37; A61N 1/371; A61N 1/37258; A61N 1/37247; A61N 2001/083
See application file for complete search history.

(56) References Cited

U.S. PATENT DOCUMENTS 4,172,459 A 10/1979 Hepp
4,552,154 A 11/1985 Hartlaub
(Continued)

FOREIGN PATENT DOCUMENTS

| WO | WO9965393 A1 | 12/1999 |
| WO | 2009114755 A2 | 9/2009 |
| WO | 2011034468 A1 | 3/2011 |

OTHER PUBLICATIONS

International Preliminary Report on Patentability issued in PCT/US2017/012641, dated Jul. 19, 2018, 9 pages.
(Continued)

*Primary Examiner* — Catherine M Voorhees
*Assistant Examiner* — Roland Dinga
(74) *Attorney, Agent, or Firm* — Faegre Drinker Biddle & Reath, LLP

(57) ABSTRACT

A system for lead integrity monitoring includes an implantable medical device (IMD) having a housing enclosing a control circuit; and a lead, having a first sensor. The lead is coupled to the housing and electrically coupled to the control circuit. The system also includes at least one processing device configured to identify a first lead failure alert based on a first set of information; obtain a second set of information generated by a second sensor; perform an evaluation of the first set of information in the context of the second set of information; and confirm or cancel the first lead failure alert based on the evaluation.

18 Claims, 3 Drawing Sheets

(52) U.S. Cl.
CPC ...... *A61N 1/37258* (2013.01); *A61N 1/37247* (2013.01); *A61N 2001/083* (2013.01)

(56) References Cited

U.S. PATENT DOCUMENTS

| | | | |
|---|---|---|---|
| 5,127,404 A | | 7/1992 | Wyborny et al. |
| 5,549,646 A | * | 8/1996 | Katz .................. A61N 1/3706 607/4 |
| 5,755,742 A | * | 5/1998 | Schuelke ............ A61N 1/3706 600/510 |
| 5,800,466 A | | 9/1998 | Routh et al. |
| 5,833,623 A | | 11/1998 | Mann et al. |
| 5,902,250 A | | 5/1999 | Verrier et al. |
| 5,904,708 A | | 5/1999 | Goedeke |
| 6,073,049 A | | 6/2000 | Alt et al. |
| 6,076,015 A | | 6/2000 | Hartley et al. |
| 6,190,324 B1 | | 2/2001 | Kieval et al. |
| 6,490,479 B2 | | 12/2002 | Bock |
| 6,804,558 B2 | | 10/2004 | Haller et al. |
| 6,890,306 B2 | | 5/2005 | Poezevera |
| 6,978,182 B2 | | 12/2005 | Mazar et al. |
| 7,146,206 B2 | | 12/2006 | Glass et al. |
| 7,395,117 B2 | | 7/2008 | Mazar et al. |
| 7,559,903 B2 | | 7/2009 | Moussavi et al. |
| 7,751,876 B2 | | 7/2010 | Healey |
| 7,996,074 B2 | | 8/2011 | Kenknight et al. |
| 8,002,553 B2 | | 8/2011 | Hatlestad et al. |
| 8,049,489 B2 | | 11/2011 | Gauglitz et al. |
| 8,108,048 B2 | | 1/2012 | Masoud |
| 8,126,548 B2 | | 2/2012 | Ding et al. |
| 8,145,590 B2 | | 3/2012 | Brockway et al. |
| 8,209,011 B2 | | 6/2012 | Freeberg |
| 8,396,543 B2 | | 3/2013 | Hoeppner et al. |
| 8,423,142 B2 | | 4/2013 | Freeberg |
| 8,611,000 B2 | | 12/2013 | Komatsu et al. |
| 8,639,318 B2 | | 1/2014 | Hatlestad et al. |
| 8,694,116 B2 | | 4/2014 | Kenknight et al. |
| 8,731,661 B2 | | 5/2014 | White |
| 8,791,815 B2 | | 7/2014 | Mazar et al. |
| 8,849,682 B2 | | 9/2014 | Mahajan et al. |
| 8,915,741 B2 | | 12/2014 | Hatlestad et al. |
| 8,929,981 B2 | | 1/2015 | Perschbacher et al. |
| 8,983,603 B2 | | 3/2015 | Perschbacher et al. |
| 9,014,807 B2 | | 4/2015 | Bocek et al. |
| 9,020,602 B2 | | 4/2015 | Aghassian |
| 9,037,240 B2 | | 5/2015 | Gunderson |
| 9,610,025 B2 | | 4/2017 | Zhang |
| 2001/0051787 A1 | | 12/2001 | Haller et al. |
| 2002/0072783 A1 | | 6/2002 | Goedeke et al. |
| 2003/0028080 A1 | | 2/2003 | Lebel et al. |
| 2005/0251227 A1 | | 11/2005 | Khoo et al. |
| 2005/0288599 A1 | | 12/2005 | MacAdam et al. |
| 2006/0265024 A1 | * | 11/2006 | Goetz ................. A61N 1/3706 607/48 |
| 2007/0255330 A1 | | 11/2007 | Lee et al. |
| 2008/0183245 A1 | | 7/2008 | Van Oort et al. |
| 2009/0058635 A1 | | 3/2009 | LaLonde et al. |
| 2009/0063187 A1 | | 3/2009 | Johnson et al. |
| 2009/0088821 A1 | | 4/2009 | Abrahamson |
| 2010/0023084 A1 | * | 1/2010 | Gunderson .......... A61N 1/3706 607/28 |
| 2010/0057167 A1 | | 3/2010 | Evers et al. |
| 2010/0152815 A1 | | 6/2010 | Vandanacker |
| 2010/0185251 A1 | | 7/2010 | Propato |
| 2010/0280841 A1 | | 11/2010 | Dong et al. |
| 2011/0270109 A1 | | 11/2011 | Zhang et al. |
| 2012/0029373 A1 | | 2/2012 | Stadler et al. |
| 2012/0078131 A1 | | 3/2012 | Zong |
| 2012/0154152 A1 | | 6/2012 | Rantala et al. |
| 2012/0158089 A1 | * | 6/2012 | Bocek ..................... A61N 1/37 607/28 |
| 2012/0165887 A1 | | 6/2012 | Lee et al. |
| 2012/0188096 A1 | | 7/2012 | Corndorf et al. |
| 2012/0232416 A1 | | 9/2012 | Gilham et al. |
| 2012/0283544 A1 | | 11/2012 | Kraetschmer et al. |
| 2012/0296228 A1 | | 11/2012 | Zhang et al. |
| 2013/0237773 A1 | | 9/2013 | An et al. |
| 2013/0274624 A1 | | 10/2013 | Mahajan et al. |
| 2014/0277243 A1 | | 9/2014 | Maskara et al. |
| 2015/0216433 A1 | | 8/2015 | Thakur et al. |
| 2015/0282738 A1 | | 10/2015 | Thakur et al. |
| 2015/0342487 A1 | | 12/2015 | Thakur et al. |
| 2016/0023013 A1 | * | 1/2016 | Greenhut ............ A61B 5/0464 600/483 |
| 2016/0045125 A1 | | 2/2016 | Krueger et al. |
| 2017/0196457 A1 | | 7/2017 | Thakur et al. |
| 2017/0196458 A1 | | 7/2017 | Ternes et al. |
| 2017/0199970 A1 | | 7/2017 | Stahmann et al. |
| 2017/0251940 A1 | | 9/2017 | Perschbacher et al. |
| 2017/0290528 A1 | | 10/2017 | Ternes et al. |

OTHER PUBLICATIONS

International Preliminary Report on Patentability issued in PCT/US2017/012649, dated Jul. 19, 2018, 10 pages.
International Preliminary Report on Patentability issued in PCT/US2017/012651, dated Jul. 19, 2018, 8 pages.
International Search Report and Written Opinion issued in PCT/US2017/012641, dated Apr. 24, 2017, 14 pages.
International Search Report and Written Opinion issued in PCT/US2017/012649, dated Mar. 29, 2017, 18 pages.
International Search Report and Written Opinion issued in PCT/US2017/012651, dated Mar. 24, 2017, 12 pages.
International Search Report and Written Opinion issued in PCT/US2017/020831, dated Jun. 16, 2017, 11 pages.
Passman, Rod S., et al. "Development and Validation of a Dual Sensing Scheme to Improve Accuracy of Bradycardia and Pause Detection in an Insertable Cardiac Monitor." Heart Rhythm, 14:1016-1023, 2017.
Sarkar, Shantanu, et al. "A Dual Sensing Scheme to Reduce Inappropriate Detection of Bradycardia and Pauses in an Insertable Cardiac Monitor." 2016 Heart Rhythm, 15 pages.

* cited by examiner

LEAD INTEGRITY MONITORING

CROSS-REFERENCE TO RELATED APPLICATION

This application claims priority to Provisional Application No. 62/322,137, filed Apr. 13, 2016, which is herein incorporated by reference in its entirety.

TECHNICAL FIELD

Embodiments of the present disclosure relate to lead integrity monitoring in implantable medical devices.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, spinal cord stimulators, vagal nerve stimulators, or other neural stimulators), cochlear implants, or drug pumps, among others.

Such IMDs can include electronic circuitry, such as to provide a desired electrostimulation, or to monitor physiologic activity. Such electronic circuitry can be coupled to an implantable lead assembly, such as including one or more electrodes or other electronic circuitry. A variety of different types of failures can affect systems including such IMDs and lead assemblies, such as including circuitry failures, electrical or mechanical coupling failures, lead dislodgement, perforation, unintentional repositioning, or failure of a conductor or electrode included as a portion of a lead assembly attached to an IMD.

Current platforms such as, for example, LATITUDE® NXT provides a "red alert" for either noise or impedance issues. For example, a right ventricular non-physiologic signal detected alert may be issued for one noisy ATP or one noisy diverted shock (e.g., the device started charging but no shock was delivered); two days with noisy sustained episodes without therapy attempt in a 30-day period. In that current context, noise may be defined as four ventricular sensed beats faster than (or equal to) 160 ms. A right ventricular pacing lead impedance abrupt change alert may be issued for three spikes relative to median in a seven-day period, where a spike >=300 ohms if median is <=750 ohms, and the spike >=750 ohms if median is >750 ohms. However, these lead checks operate on data which is collected just once per day.

SUMMARY

In an Example 1, a system, comprising: an implantable medical device (IMD) configured to be implanted within a patient's body, the IMD comprising: a housing enclosing a control circuit; and a lead, having a first sensor, wherein the lead is coupled to the housing and electrically coupled to the control circuit; and at least one processing device configured to: identify a first lead failure alert, the first lead failure alert comprising an indication of a potential lead failure based on a first set of information satisfying an alert criterion; obtain a second set of information generated by a second sensor; perform an evaluation of the first set of information in the context of the second set of information; and confirm or cancel the first lead failure alert based on the evaluation.

In an Example 2, the system of Example 1, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

In an Example 3, the system of Example 2, the first set of information comprising a first set of impedance data associated with the lead, wherein the at least one processing device is configured to perform the evaluation by: determining whether a subset of the first set of impedance data satisfies the alert criterion, wherein the subset of the first set of impedance data corresponds to at least one instance of a fixed value of the second set of information; wherein the processing device is configured to confirm the first lead failure alert if the subset of the first set of impedance data satisfies the alert criterion.

In an Example 4, the system of Example 2, the first set of information comprising a first set of impedance data associated with the lead, wherein the at least one processing device is configured to perform the evaluation by: determining a variability of a subset of the first set of impedance data, wherein the subset of the first set of impedance data corresponds to a plurality of instances of a fixed value of the second set of information; wherein the processing device is configured to confirm the first lead failure alert if the variability exceeds a variability threshold.

In an Example 5, the system of Example 2, the first set of information comprising a first set of impedance data associated with the lead, wherein the first lead failure alert is generated in response to a determination that a first variability exceeds a variability threshold, the first variability comprising a variability of the first set of impedance data, wherein the at least one processing device is configured to perform the evaluation by: determining a second variability, the second variability comprising a variability of a subset of the first set of impedance data, wherein the subset of the first set of impedance data corresponds to a plurality of instances of a fixed value of the second set of information; and determining a difference between the first variability and the second variability, wherein the processing device is configured to cancel the first lead failure alert if the difference exceeds a difference threshold.

In an Example 6, the system of Example 2, the first set of information comprising a first set of impedance data associated with the lead, wherein the at least one processing device is configured to perform the evaluation by: determining a variability of a subset of the first set of impedance data, wherein the subset of the first set of impedance data corresponds to a first extreme value of the second set of information and a second extreme value of the second set of information; wherein the processing device is configured to confirm the first lead failure alert if the variability exceeds a variability threshold.

In an Example 7, the system of any of Examples 2-6, wherein the first set of impedance data is obtained using a first sampling frequency, and wherein, in response to receiving the first lead failure alert, the at least one processing device is configured to obtain a second set of impedance data using a second sampling frequency, wherein the second sampling frequency is higher than the first sampling frequency.

In an Example 8, the system of any of Examples 1-7, wherein the second set of information comprises at least one of posture data associated, respiratory data, cardiac cycle data, lead strain data, arm displacement data, and a second set of impedance data, wherein the second set of impedance data is associated with an additional lead.

In an Example 9, the system of any of Examples 1-8, wherein the at least one processing device is configured to confirm the first lead failure alert by generating a second lead failure alert, the second lead failure alert comprising an instruction configured to cause a display device to present an indication of failure of the lead.

In an Example 10, the system of any of Examples 1-9, wherein the at least one processing device is configured to: determine a number of first lead failure alerts received within a specified time period; determine a number of the first lead failure alerts received within the specified time period that were canceled; determine that the number of the first lead failure alerts received within the specified time period that were canceled exceeds an alert threshold; and adjust the alert criterion in response to determining that the number of the first lead failure alerts received within the specified time period that were canceled exceeds the alert threshold.

In an Example 11, a method of monitoring a status of a lead of an implantable medical device (IMD), the method comprising: identifying a first lead failure alert, the first lead failure alert comprising an indication of a potential lead failure based on a first set of information satisfying an alert criterion; obtaining a second set of information generated by a second sensor; performing an evaluation of the first set of information in the context of the second set of information; and confirming or canceling the first lead failure alert based on the evaluation.

In an Example 12, the method of Example 11, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

In an Example 13, the method of Example 12, the first set of information comprising at least one of a first set of impedance data associated with the lead, wherein performing the evaluation comprises: determining whether a subset of the first set of impedance data satisfies the alert criterion, wherein the subset of the first set of impedance data corresponds to at least one instance of a fixed value of the second set of information; and confirming the first lead failure alert if the subset of the first set of impedance data satisfies the alert criterion.

In an Example 14, the method of Example 12, the first set of information comprising at least one of a first set of impedance data associated with the lead, wherein the first lead failure alert is generated in response to a determination that a first variability exceeds a variability threshold, the first variability comprising a variability of the first set of impedance data, wherein performing the evaluation comprises: determining a second variability, the second variability comprising a variability of a subset of the first set of impedance data, wherein the subset of the first set of impedance data corresponds to a plurality of instances of a fixed value of the second set of information; determining a difference between the first variability and the second variability; and canceling the first lead failure alert if the difference exceeds a difference threshold.

In an Example 15, the method of any of Examples 11-14, wherein the second set of information comprises at least one of posture data, respiratory data, cardiac cycle data, strain data, displacement data, and a second set of impedance data, wherein the second set of impedance data is associated with an additional lead.

In an Example 16, a system for monitoring lead integrity, comprising: an implantable medical device (IMD) configured to be implanted within a patient's body, the IMD comprising: a housing enclosing a control circuit; and a lead, having a first sensor, wherein the lead is coupled to the housing and electrically coupled to the control circuit; and at least one processing device configured to: identify a first lead failure alert, the first lead failure alert comprising an indication of a potential lead failure based on a first set of information satisfying an alert criterion; obtain a second set of information generated by a second sensor; perform an evaluation of the first set of information in the context of the second set of information; and confirm or cancel the first lead failure alert based on the evaluation.

In an Example 17, the system of Example 16, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

In an Example 18, the system of Example 17, the first set of information comprising at least one of a first set of impedance data associated with the lead, wherein the at least one processing device is configured to perform the evaluation by: determining whether a subset of the first set of impedance data satisfies the alert criterion, wherein the subset of the first set of impedance data corresponds to at least one instance of a fixed value of the second set of information; wherein the processing device is configured to confirm the first lead failure alert if the subset of the first set of impedance data satisfies the alert criterion.

In an Example 19, the system of Example 17, the first set of information comprising at least one of a first set of impedance data associated with the lead, wherein the at least one processing device is configured to perform the evaluation by: determining a variability of a subset of the first set of impedance data, wherein the subset of the first set of impedance data corresponds to a plurality of instances of a fixed value of the second set of information; wherein the processing device is configured to confirm the first lead failure alert if the variability exceeds a variability threshold.

In an Example 20, the system of Example 17, the first set of information comprising at least one of a first set of impedance data associated with the lead, wherein the first lead failure alert is generated in response to a determination that a first variability exceeds a variability threshold, the first variability comprising a variability of the first set of impedance data, wherein the at least one processing device is configured to perform the evaluation by: determining a second variability, the second variability comprising a variability of a subset of the first set of impedance data, wherein the subset of the first set of impedance data corresponds to a plurality of instances of a fixed value of the second set of information; and determining a difference between the first variability and the second variability, wherein the processing device is configured to cancel the first lead failure alert if the difference exceeds a difference threshold.

In an Example 21, the system of Example 17, the first set of information comprising at least one of a first set of impedance data associated with the lead, wherein the at least one processing device is configured to perform the evaluation by: determining a variability of a subset of the first set of impedance data, wherein the subset of the first set of impedance data corresponds to a first extreme value of the second set of information and a second extreme value of the second set of information; wherein the processing device is configured to confirm the first lead failure alert if the variability exceeds a variability threshold.

In an Example 22, the system of Example 17, the first set of information comprising at least one of a first set of impedance data associated with the lead, wherein the first set of impedance data is obtained using a first sampling frequency, and wherein, in response to receiving the first lead failure alert, the at least one processing device is configured to obtain a second set of impedance data using a second sampling frequency, wherein the second sampling frequency is higher than the first sampling frequency.

In an Example 23, the system of Example 17, wherein the second set of information comprises at least one of posture data associated, respiratory data, cardiac cycle data, lead strain data, arm displacement data, and a second set of impedance data, wherein the second set of impedance data is associated with an additional lead.

In an Example 24, the system of Example 17, wherein the at least one processing device is configured to confirm the first lead failure alert by generating a second lead failure alert, the second lead failure alert comprising an instruction configured to cause a display device to present an indication of failure of the lead.

In an Example 25, the system of Example 17, wherein the at least one processing device is configured to: determine a number of first lead failure alerts received within a specified time period; determine a number of the first lead failure alerts received within the specified time period that were canceled; determine that the number of the first lead failure alerts received within the specified time period that were canceled exceeds an alert threshold; and adjust the alert criterion in response to determining that the number of the first lead failure alerts received within the specified time period that were canceled exceeds the alert threshold.

In an Example 26, a system for monitoring lead integrity, comprising: an implantable medical device (IMD) configured to be implanted within a patient's body, the IMD comprising: a housing enclosing a control circuit; a lead, having a first sensor, wherein the lead is coupled to the housing and electrically coupled to the control circuit, wherein the control circuit is configured to obtain a first set of impedance data associated with the lead; and a first communication component configured to transmit the first set of impedance data; and an external monitoring device (EMD) configured to be disposed outside of the patient's body, the EMD comprising: a second communication component configured to receive, from the first communication component, the first set of impedance data; and a processing device configured to (1) identify a first lead failure alert, the first lead failure alert comprising an indication of a potential lead failure based on a first set of information satisfying an alert criterion, the first set of information comprising the first set of impedance data associated with the lead; (2) obtain a second set of information generated by a second sensor; (3) perform an evaluation of the first set of information in the context of the second set of information; and (4) confirm or cancel the first lead failure alert based on the evaluation.

In an Example 27, the system of Example 26, wherein the second sensor comprises at least one of an accelerometer, a sensor disposed on an additional lead coupled to the housing, a displacement sensor configured to detect arm movement, a strain sensor configured to detect tension in the lead, a respiration sensor, and a heart rate sensor.

In an Example 28, a method of monitoring a status of a lead of an implantable medical device (IMD), the method comprising: identifying a first lead failure alert, the first lead failure alert comprising an indication of a potential lead failure based on a first set of information satisfying an alert criterion; obtaining a second set of information generated by a second sensor; performing an evaluation of the first set of information in the context of the second set of information; and confirming or canceling the first lead failure alert based on the evaluation.

In an Example 29, the method of Example 28, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

In an Example 30, the method of Example 29, the first set of information comprising at least one of a first set of impedance data associated with the lead, wherein performing the evaluation comprises: determining whether a subset of the first set of impedance data satisfies the alert criterion, wherein the subset of the first set of impedance data corresponds to at least one instance of a fixed value of the second set of information; and confirming the first lead failure alert if the subset of the first set of impedance data satisfies the alert criterion.

In an Example 31, the method of Example 29, the first set of information comprising at least one of a first set of impedance data associated with the lead, wherein the first lead failure alert is generated in response to a determination that a first variability exceeds a variability threshold, the first variability comprising a variability of the first set of impedance data, wherein performing the evaluation comprises: determining a second variability, the second variability comprising a variability of a subset of the first set of impedance data, wherein the subset of the first set of impedance data corresponds to a plurality of instances of a fixed value of the second set of information; determining a difference between the first variability and the second variability; and canceling the first lead failure alert if the difference exceeds a difference threshold.

In an Example 32, the method of Example 29, the first set of information comprising at least one of a first set of impedance data associated with the lead, wherein the second set of information comprises at least one of posture data, respiratory data, cardiac cycle data, strain data, displacement data, and a second set of impedance data, wherein the second set of impedance data is associated with an additional lead.

In an Example 33, the method of Example 29, wherein the first set of impedance data is obtained using a first sampling frequency, the method further comprising obtaining, in response to receiving the first lead failure alert, the second set of information using a second sampling frequency, wherein the second sampling frequency is higher than the first sampling frequency.

In an Example 34, the method of Example 29, wherein confirming the first lead failure alert comprises generating a second lead failure alert, the second lead failure alert comprising an instruction configured to cause a display device to present an indication of failure of the lead.

In an Example 35, the method of Example 29, further comprising: determining a number of first lead failure alerts received within a specified time period; determining a number of the first lead failure alerts received within the specified time period that were canceled; determining that the number of the first lead failure alerts received within the specified time period that were canceled exceeds an alert threshold; and adjusting the alert criterion in response to determining that the number of the first lead failure alerts received within the specified time period that were canceled exceeds the alert threshold.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
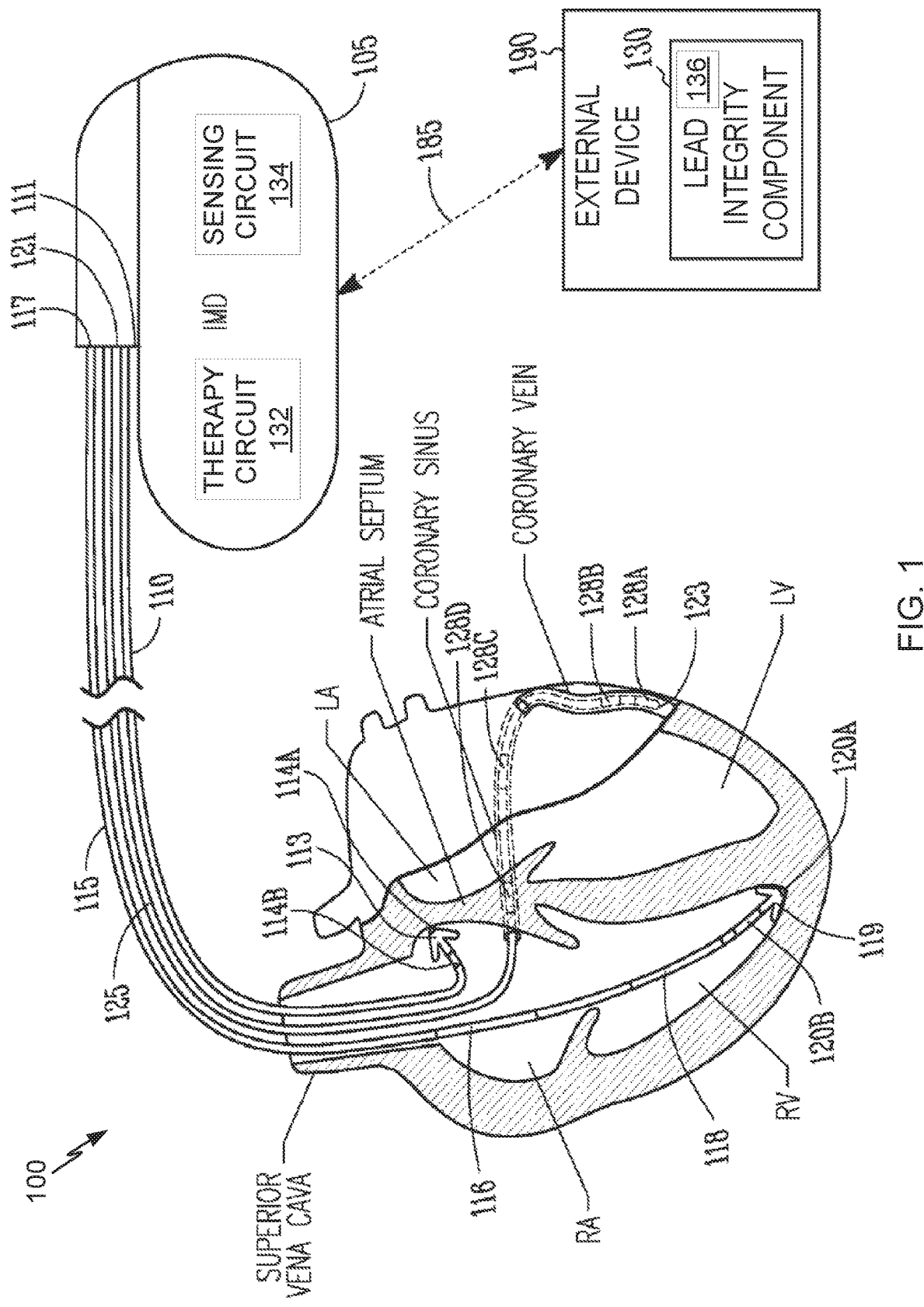
FIG. 1 shows a medical system, in accordance with certain embodiments of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Embodiments of the subject matter disclosed herein include a system having an implantable medical device (IMD) configured to be implanted within a patient's body. The IMD may be any type of medical device that includes at least a portion of a component that is configured to be implanted within a patient's body. For example, the IMD may include a subcutaneous lead and/or a transcutaneous lead. The IMD may include a housing enclosing a control circuit. The housing may be implantable or external. The lead, which is communicatively coupled to the control circuit, may be coupled to the housing and electrically coupled to the control circuit. In embodiments, the lead may be wirelessly coupled to the control circuit.

The system also may include at least one processing device. The at least one processing device may include one or more processing devices disposed in an implantable housing and/or one or more processing devices disposed in an external housing. In embodiments, one or more processing devices may be disposed in an external device that is separate from, but communicatively coupled to, the IMD. By using some combination of operations, the at least one processing device may be configured to identify a first lead failure alert. The first lead failure alert may include an indication of a potential lead failure based on a first set of information satisfying an alert criterion. The at least one processing device may be configured to obtain, in response to identifying the first lead failure alert, a second set of information generated by a second sensor; perform an evaluation of the first set of information in the context of the second set of information; and confirm or cancel the first lead failure alert based on the evaluation.

According to embodiments, the IMD may include any type of IMD, any number of different components of an implantable system, and/or the like. For example, the IMD may include a control device, a monitoring device, a pacemaker, an implantable cardioverter defibrillator (ICD) (e.g., a subcutaneous ICD (S-ICD)), a cardiac resynchronization therapy (CRT) device and/or the like, and may be an implantable medical device known in the art or later developed, for providing therapy and/or diagnostic data about a patient and/or the IMD. In various embodiments, the IMD may include both defibrillation and pacing/CRT capabilities (e.g., a CRT-D device). In embodiments, the IMD may include a neuromodulation device such as, for example, a spinal cord stimulator, a deep brain stimulator, a sacral nerve stimulator, and/or the like.

FIG. 1 shows a medical system 100, including an IMD 105 and an external device 190, with a wireless data connection, telemetry link 185, between IMD 105 and external device 190. In this example of FIG. 1, medical system 100 is a cardiac rhythm management (CRM) system 100. IMD 105 is electrically coupled to a heart through implantable leads 110, 115, and 125. External device 190 communicates with IMD 105 via telemetry link 185. Although the IMD 105 depicted in FIG. 1 is described herein as a CRM system 100, aspects of embodiments of the lead failure detection and analysis concepts described herein with reference to IMD 105 may be applied to any number of other types of IMDs, as described above.

IMD 105 includes a hermetically sealed can that houses control electronics including an electronic circuit that senses physiological signals and delivers therapeutic electrical pulses. The hermetically sealed can may also function as a can electrode for sensing and/or pulse delivery purposes. IMD 105 may sense one or more cardiac signals, including signals indicative of one or more arrhythmia episodes, and may generate cardiac data representative of the one or more cardiac signals. For example, the control electronics of IMD 105 may sense and store one or more cardiac signals on a continuous basis as facilitated by the higher data storage capacities provided by the rapid improvements in semiconductor technologies. Additionally or alternatively, IMD 105 may store one or more cardiac signals on an episodic basis. In one example, IMD 105 includes a pacemaker that delivers cardiac pacing therapies. In another example, IMD 105 includes a pacemaker and a cardioverter/defibrillator that delivers cardioversion/defibrillation therapies. In various examples, IMD 105 includes one or more devices selected from monitoring devices and therapeutic devices such as a pacemaker, a cardioverter/defibrillator, a neurostimulator, a drug delivery device, and a biological therapy device.

Lead 110 is a right atrial (RA) pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations and delivering RA pacing pulses.

Lead 115 is a right ventricular (RV) pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations and delivering RV pacing pulses. In various examples, proximal defibrillation electrode 116 and/or distal defibrillation electrode 118 may also be used for sensing the RV electrogram.

Lead 125 is a left ventricular (LV) coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes an LV tip electrode 128A, a distal LV ring electrode 128B, and two proximal LV ring electrodes 128C and 128D. The distal portion of lead 125 is configured for placement in the coronary sinus and coronary vein such that LV electrodes 128A and 128B are placed in the coronary vein, and LV electrodes 128C and 128D are placed in or near the coronary sinus. LV electrodes 128A and 128B are incorporated into the lead body at distal end 123 and are each electrically coupled to IMD 105 through a conductor extending within the lead body. LV tip electrode 128A, distal LV ring electrode 128B, proximal LV ring electrode 128C, proximal LV ring electrode 128D, and/or the can electrode allow for sensing an LV electrogram indicative of LV depolarizations and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs.

In some examples, a wireless sensing and/or therapy system may be used in which, for example, IMD 105 communicates with one or more other implanted devices to facilitate sensing and/or delivering therapy. For example, in embodiments, IMD 105 may be configured to communicate with, and control, one or more leadless pacing seeds implanted in or near the heart. In various examples, IMD 105 senses the one or more cardiac signals using any combination of electrodes, such as those illustrated in FIG. 1, suitable for detection and classification of the one or more arrhythmia episodes.

As indicated above, the leads 110, 115, and 125 can include one or more internal conductors, such as one or more linear or coiled conductor shapes. Such conductors can fail, such as fracturing, separating, shorting out, becoming electrically "leaky." Various defects can include providing an unacceptably low impedance between conductors, or between a conductor and surrounding tissue (e.g., forming a "sneak path" back to the can), etc. Such failures can be transient or continuous.

In an example, the IMD 105 can include a therapy circuit 132 that can be electrically coupled to one or more conductors included in one or more of the leads 110, 115, and 125, configured to provide one or more of a voltage or current excitation pulse to the conductor. In an example, the IMD 105 can include a sensing circuit 134 that can be configured to detect a voltage or current developed in response to the excitation provided by the therapy circuit 132. The sensing circuit may also include sensors such as posture sensors, activity sensors, heart sound sensors, and/or the like.

In embodiments, for example, the therapy or sensing circuits 132, 134 may measure and determine a first set of information (e.g., impedance data), which may indicate that a lead is failing or has failed. For example, the first set of impedance data may include two or more lead impedance measurements corresponding to at least approximately the same phase of the cardiac cycle, where the two times are separated enough to capture an artifact. Based on the first set of impedance data satisfying one or more alert criteria (e.g., detecting a step change in the first set of impedance data), the therapy or sensing circuits may initiate a first lead failure alert Examples of systems and methods for identifying the first lead failure alert are described in U.S. Pat. No. 9,014,807, assigned to Cardiac Pacemakers, Inc., of St. Paul, Minn., the entirety of which is hereby incorporated herein by reference. Upon identifying a first lead failure alert, the first set of impedance data may be evaluated in the context of a second set of information to confirm or cancel the first lead failure alert.

In embodiments, upon receiving or initiating the first lead failure alert, impedance information and/or other information (e.g., information obtained by the sensing circuit 134) relating to leads may be captured within the IMD 105 and/or transmitted to an external device 190 for evaluation. For example, the transmitted information may be analyzed by the external device 190 in context of other physiological information to determine whether a lead has or is failing. In other embodiments, the IMD 105 may do a part, or all of the analysis. External device 190 may include a programmer and/or other components of a patient monitoring system such as, for example, a repeater, a cellular phone, a computing device, and/or the like. External device 190 may include an external therapy and/or sensing device such as, for example, a wearable defibrillator, an external cardiac monitor, and/or the like. External device 190 allows for programming of IMD 105 as well as diagnostic analysis of physiological sensor data and may receive data from IMD 105 representative of signals acquired by IMD 105 via telemetry link 185.

Telemetry link 185 provides for data transmission from IMD 105 to external device 190. Data transmission from IMD 105 to external device 190 may include, for example, physiological data acquired by and stored in IMD 105, therapy history data stored in IMD 105, and data indicating an operational status of IMD 105 (e.g., battery status and lead impedance). The physiological data include the cardiac data representative of the one or more cardiac signals. In some embodiments, the physiologic data can also be obtained and transmitted from the external device 190.

Telemetry link 185 also provides for data transmission from external device 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing tachyarrhythmia detection) and programming IMD 105 to deliver pacing and/or cardioversion/defibrillation therapies.

Telemetry link 185 may include an inductive telemetry link, a far-field radio-frequency telemetry link, another data transfer link or a combination of multiple data transfer links. Telemetry link 185 occurs transcutaneously, i.e., through the patient's tissue, making it particularly useful in a medical implantable device system. For an inductive telemetry link close proximity and proper orientation between the antennas for IMD 105 and external device 190 and will generally improve the coupling between them, but deviation from ideal orientations can still result in suitably reliable data transfer. In any event, as compared to RF wireless communication techniques, and inductive telemetry link may provide lower power consumption for a given volume of data, but may also be more inconvenient for a patient as the external device is secured in close proximity with the internal device during the data transfer. In embodiments, the data transfer link may vary according to a quantity of data to be transferred between IMD 105 and external device 190.

The term "telemetry link" may refer to an ability to communicate some type of information in at least one direction between at least two devices, and should not be understood to be limited to a direct, persistent, or otherwise limited communication channel. That is, according to some examples, the telemetry link 185 may be a persistent communication link, an intermittent communication link, an ad-hoc communication link, and/or the like. The telemetry link 185 may refer to direct communications between IMD 105 and external device 190, and/or indirect communications that travel between IMD 105 and external device 190 via at least one other device (e.g., a repeater, router, hub, cell phone and/or the like). The telemetry link 185 may facilitate uni-directional and/or bi-directional communication between the IMD 105 and external device 190.

External device 190 includes a lead integrity component 130 that identifies a first lead failure alert and performs an evaluation of information obtained from IMD 105 to confirm or cancel the first lead failure alert. Although the lead integrity component 130 is shown as being implemented within the external device 190, the lead integrity component 130 and its functions may be implemented within the IMD 105. In embodiments, lead integrity component 130 identifies the first lead failure alert by evaluating a first set of information. In other embodiments, the lead integrity component 130 identifies the first lead failure alert by receiving an indication of the first lead failure alert from another component of the external device 190 and/or the IMD 105. Lead integrity component 130 further may include computer-readable memory 136 for storing data received from an IMD, such as the continuous or episodic cardiac signals from IMD 105.

The circuit(s) of the CRM system 100 may be implemented using a combination of hardware, software, and/or firmware. In various examples, each element of IMD 105 and external device 190, including its various examples, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof. For example, lead integrity component 130 may include a set of computer-executable instructions stored in a memory that, when executed by a processor, causes the processor to perform aspects of embodiments of the functionality of the lead integrity component 130 described herein.

In embodiments, the memory includes computer-readable media in the form of volatile and/or nonvolatile memory and may be removable, nonremovable, or a combination thereof. The memory may include non-transitory computer-readable media. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. The computer-executable instructions may include, for example, computer code, machine-usable instructions, and the like such as, for example, program components capable of being executed by one or more processors. Program components may be programmed using any number of different programming environments, including various languages, development kits, frameworks, and/or the like.

Figure 2:
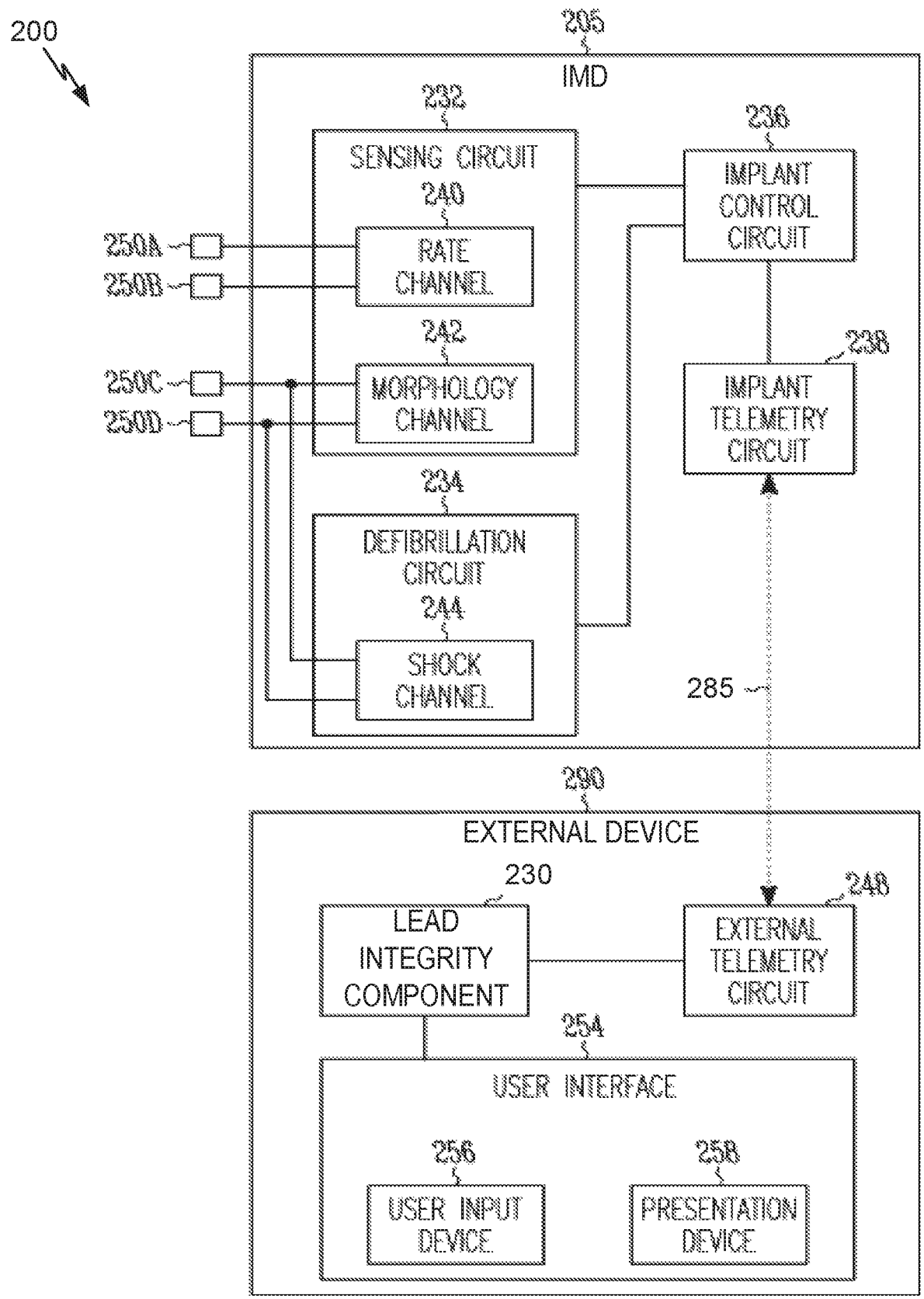
FIG. 2 shows a block diagram illustrating portions of a circuit of an IMD and portions of a circuit of an external device of a medical system, in accordance with certain embodiments of the present disclosure.

FIG. 2 is a block diagram illustrating an example of portions of a circuit of IMD 205 and portions of a circuit of an external device 290 of a medical system 200. IMD 205 represents an example of IMD 105 and includes a sensing circuit 232, a defibrillation circuit 234, control electronics including an implant control circuit 236, and an IMD communication module 238. In embodiments, for example, IMD 205 is an implantable cardioverter defibrillator (ICD). In other embodiments, IMD 205 may be, or include, a monitoring device, a pacemaker, or a cardiac resynchronization therapy (CRT) device. In embodiments, IMD 205 may include both defibrillation and pacing/CRT capabilities (e.g., a CRT-D device). Sensing circuit 232 includes a rate channel 240 and a morphology channel 242. Rate channel 240 senses a regional cardiac signal through electrodes 250A and 250B for use in heart beat detection. Morphology channel 242 senses a global cardiac signal through electrodes 250C and 250D for use in morphological analysis.

In some examples, rate channel 240 senses a regional ventricular electrogram through an RV tip electrode such as electrode 120A and an RV coil electrode such as electrode 118, and morphology channel 242 senses a global ventricular electrogram through the RV coil electrode and an SVC coil electrode such as electrode 116. In this example, electrode 250A is the RV tip electrode, electrodes 250B and 250C are the same RV coil electrode, and electrode 250D is the SVC coil electrode. In the same or different examples, the SVC coil electrode is electrically connected to the can electrode.

Defibrillation circuit 234 includes a shock channel 244 to deliver cardioversion/defibrillation pulses (shocks). In the illustrated example, shock channel 244 delivers the shocks using the same pair of electrodes as used by morphology channel 242 (so the "morphology channel" is also referred to as the "shock channel"). In an alternative example, a single cardiac signal is sensed for use in heart rate detection and morphology analysis, such as through electrodes 250C and 250D. While this alternative example eliminates the need for sensing two cardiac signals, the example as illustrated in FIG. 2 provides for more robust heart beat detection. Implant control circuit 236 controls the operation of IMD 205 including the sensing of the one or more cardiac signals and the delivery of the shocks. Implant control circuit 236 also includes the physical IMD memory, a non-transitory computer-readable memory, for storing the one or more continuous or episodic cardiac signals. IMD communication module 238 supports the functions of telemetry link 285, including transmitting the cardiac data from IMD 205 to external device 290.

External device 290 represents an example of external device 190 and may represent a hand-held programmer or a clinician's programmer. External device 190 includes lead integrity component 230, an external telemetry circuit 248, and a user interface 254. Implant telemetry circuit 248 supports the functions of telemetry link 285, including receiving the cardiac data transmitted from IMD 205. User interface 254 includes a user input device 256 and a presentation device 258. User input device 256 receives various commands and parameters from the user for controlling operations of IMD 205 and external device 290. Presentation device 258 presents various patient and device information including an indication of failure of a lead, e.g., in the event that the lead integrity component 230 confirms a first lead failure alert. User interface 254 may be similar to that used for a computer, cell phone, or other hand held electronic device, and may include touchable buttons and a display for example, allowing a user, such as a clinician, to operate the external device 290.

In embodiments, a high day to day variability in lead impedance may constitute a trigger event that results in implementation of a study prescription that gathers high temporal resolution impedance data as well as other sensor data such as posture data to facilitate determining whether the impedance variability is due to posture changes or a broken lead. Study prescriptions refer to sets of instructions, conditions, protocols, and/or the like, that specify one or more of an information gathering scheme and a communication scheme, and may be configured, for example, to obtain information at a resolution sufficient for performing a certain analysis (e.g., associated with a diagnostic model), while managing the resulting impact to device longevity and/or performance. Examples of systems and methods for facilitating high-resolution gathering are described in U.S. Provisional Patent Application No. 62/276,383, to D. Ternes et al., filed on Jan. 8, 2016, the entirety of which is hereby incorporated herein by reference. In some embodiments, the first alert can automatically trigger the second stage collection of high resolution impedance data as well as other sensor data.

In embodiments, data may be obtained from an IMD by triggering a limited-time system behavior change. Further embodiments include utilizing study prescriptions that specify one or more criteria, procedures, parameters, and/or other aspects of obtaining the data. For example, study prescriptions may facilitate enabling sensor components, obtaining data, analyzing data, batching data obtained by an IMD, communicating the batched data to an external device, reconstructing the batched data at the external device, and/or the like.

Study prescriptions may also include instructions for configuring one or more sensors, modifying one or more filters, modifying one or more sensor inputs (e.g. by changing a vector measured by a minute volume (MV) impedance component from focusing on changes in a lung to focusing on stroke volume of the heart), modifying one or more sensing parameters (e.g., sampling rate, sample storage rate, sensing thresholds, sensing durations, etc.), and/or the like.

According to embodiments, existing lead check processes may be used to trigger a higher resolution data dump, e.g., following a first lead failure alert. In embodiments, a user (e.g., a clinician) may order a lead integrity study or the device (or another, communicatively coupled device) may order the study. In embodiments, an IMD may be continuously (or continually) collecting information that may be used to assess lead integrity such as, for example, impedance data and another type of data (e.g., posture information, impedance measured on electrodes on another lead, and/or the like). Upon detection of a trigger event (e.g., a lead failure indication), the IMD (or another device) may be configured to analyze the lead's the impedance data in the context of the other data (e.g., the posture data). Depending on the results of the analysis, the alert may be discontinued or sustained (e.g., if the analysis meets specified criteria).

For example, if impedance information is analyzed in the context of posture information, an analysis component may determine whether impedance variations can be accounted for by the posture information. If so, it may be determined that the lead is not broken, and if not, it may be determined that the lead is broken. In embodiments, impedance variations may be analyzed in the context of other impedances, and/or to determine whether the impedance variations are cyclic (e.g., representing an expected circadian variation of impedance). In embodiments, evaluation of impedance data in the context of posture data includes comparing the variability in the impedance sensor at a fixed posture, and discontinuing the alert if the difference in the variability at the fixed posture and the impedance variability that resulted in the alert exceeds a threshold. In embodiments, evaluation of impedance data in the context of posture data includes comparing the variability in the impedance sensor at a fixed posture, and sustaining the alert if the variability is exceeds a pre-specified threshold. Any number of other techniques for analyzing the impedance data in the context of posture information may be used for confirming lead integrity.

In embodiments, analyzing the impedance data that results in the initial alert (first impedance data) in the context of impedance measured using electrodes on a lead other than the lead used for the impedance data underlying the initial alert (second impedance data) includes determining a correlation between the first impedance data and second impedance data and discontinuing the initial alert if the correlation exceeds a threshold. In embodiments, analyzing the impedance data that results in the initial alert (first impedance data) in the context of impedance measured using electrodes on a lead other than the lead used for the impedance data underlying the initial alert (second impedance data) includes measuring the first impedance data only when the second impedance data is within a very narrow range, and discontinuing the initial alert if the variability of first impedance measurements constrained by the second impedance is below a threshold. Any number of other techniques for analyzing the impedance data in the context of impedance data from other leads may be used for confirming lead integrity.

The lead integrity study may include, for example, data collection corresponding to sensor "state" transitions (e.g., posture transitions), which may be sorted by sensor "states." In embodiments, this data collection may be automatic high-rate data collection. In an example, if the data is obtained from a posture sensor, the IMD may automatically sort impedance data by different postures. In embodiments, data collection may include impedance data from different vectors that do not involve the suspect lead. This data may be used as a confirmation for lead integrity. Embodiments may include performing high resolution lead integrity monitoring for a certain number of weeks after implant to alert to lead dislodgment.

Additionally, embodiments may be configured to facilitate differentiation between lead fracture and lead dislodgement. For example, high variability at a controlled posture may suggest lead fracture; and high variability using a tip vector may suggest lead dislodgement. In embodiments, the study prescription may cause the IMD to perform a higher-rate lead check when the patient is moving his or her arms while otherwise inactive. Since MV is affected by this arm movement, that could be the "sensor" for arm movement, particularly if the lead check is performed with a slow-moving arm swing from straight above the head down to the arms along the side.

Figure 3:
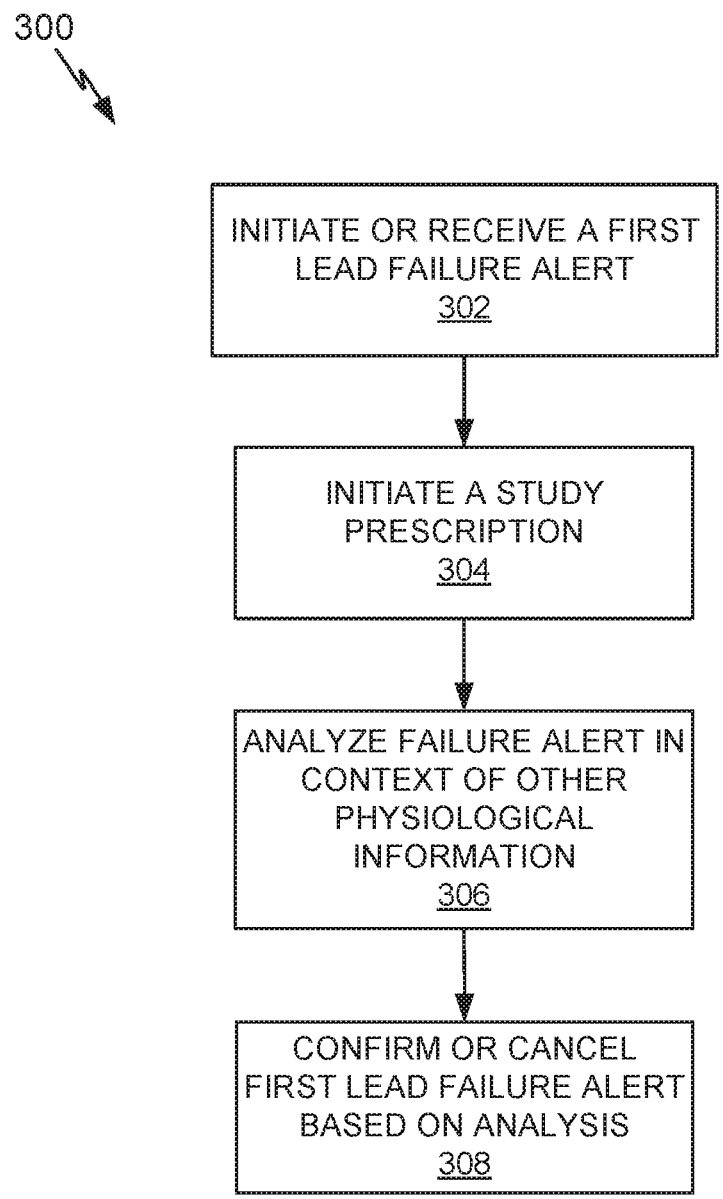
FIG. 3 shows a flow diagram depicting an illustrative method of monitoring a status of a lead of an IMD, in accordance with certain embodiments of the present disclosure.

FIG. 3 is a flow diagram depicting an illustrative method 300 of monitoring a status of a lead of an implantable medical device (IMD), in accordance with embodiments of the disclosure. According to embodiments, the IMD may be, be similar to, include, or be included in, IMD 105 depicted in FIG. 1 and/or the IMD 205 depicted in FIG. 2. Each of the illustrative steps and functions may be carried out individually or shared by an IMD and/or external device.

Embodiments of the method 300 include initiating or receiving a first lead failure alert (block 302), which could indicate potential lead failure, lead fracture, lead dislodgement, lead perforation, lead repositioning. The first lead failure alert may include an indication of a potential lead failure based on a first set of information, e.g., a first set of impedance data, associated with the lead satisfying an alert criterion. In embodiments, the first set of information may include user input (e.g., clinician-initiated input such as input indicating that a lead failure may exist). In embodiments, the first set of information may include a set of sensed noise information, where the first lead failure alert may be determined based on an evaluation of a rate of occurrence of sensed noise where the sensed noise could be due to intermittent lead integrity failure, lead dislodgement, and/or perforation.

In embodiments, the first set of information may include a set of pace capture information, where the first lead failure alert may be determined based on a change in percentage pace capture as compared, for example, to a baseline pace capture percentage, which may include a certain pace capture percentage or a metric, which may be, a long term average (where, e.g., lead dislodgement or repositioning may impact pacing capture, even where lead impedance measurements may not indicate a potential failure), or a short term average (where, e.g., position and/or posture changes may impact pacing capture). In embodiments, for example, a long term average may be calculated over a time period of approximately an hour or more, while a short term average may be calculated over a time period of approximately an hour or less. Similarly, in embodiments, the first set of information may include a change in a pace capture threshold as compared to a baseline pace capture threshold, a long term average, or a short term average.

In embodiments, the first set of information may include a set of sensed intrinsic information, where the first lead failure alert may be determined based on a change in a sensing pattern (e.g., changes in intrinsic signal patterns resulting from loss of capture) which may be due to intermittent fracture of leads, floating leads, and/or the like. The changes in sensing patterns may include, for example, certain amounts of variability or other identifiable characteristics. In embodiments, the first set of information may include a set of tachycardia episode information, where the first lead failure alert may be determined based on a certain number of non-sustained tachycardia episodes within a certain time period, and/or an increase in a number of non-sustained tachycardia episodes (which may be due, e.g., to oversensing by a dislodged lead or to intermittent lead integrity failure). In embodiments, the first set of information may include a set of phrenic nerve stimulation, where the first lead failure alert may be determined based on a change in phrenic nerve stimulation.

For example, circuitry in an IMD or external device may compare impedance data with predetermined or expected impedance characteristics and indicate via an alert that a lead is failing or has failed. The IMD or external device may initiate the alert or receive the alert from the other.

The method 300 may further include initiating a study prescription (block 304). Study prescriptions may include instructions that detail what and how information should be collected and communicated. For example, a study prescription may instruct an IMD and/or external device to gather certain physiological information in a given range of time and the information may be gathered at a resolution different than an IMD and/or external device typical operating resolution. In embodiments, information measured by sensors is gathered, packaged, and transmitted to an IMD and/or external device. Example sensor and measured information includes displacement sensors that indicate arm movement, posture sensors that indicate a patient's posture, strain sensors that indicate tension of a lead, respiration sensors (e.g., MV sensors) that indicate certain respiratory conditions, and heart rate sensors. In embodiments, impedance information measured by other leads or vectors is gathered, packaged, and transmitted to an IMD and/or external device. The sensed information can be stored in memory of an IMD or external device or stored in a central repository like a server. The sensed information may be automatically transmitted to another device upon a first lead failure alert or transmission may be initiated by other criteria, for example, upon request by a physician.

The method may further include analyzing the lead impedance data in the context of the second set of information like other physiological information mentioned above (block 306) and based on the analysis, confirming or canceling the first lead failure alert based on the analysis (block 308).

In some embodiments, if the second set of information includes posture information, analysis of the lead failure alert may mean comparing the variability in the impedance sensor at a fixed posture, and the first alert is cancelled if the variability is substantially less than the impedance variability that drove the first alert. This analysis may indicate that the lead failure alert was triggered by a patient's posture causing the lead to measure impedance below a predetermined threshold.

In some embodiments, if the second set of information includes posture information, analysis of the lead failure alert may mean comparing the variability in the impedance sensor at a fixed posture or sets of extreme postures (e.g., extreme displacement of arms and/or shoulders), and the first alert is confirmed if the variability exceeds a pre-specified threshold. This analysis may indicate that the lead failure alert was not triggered by a patient's posture and therefore the lead may be failing.

In some embodiments, if the second set of information includes impedance measured using electrodes on a lead other than the at-issue lead, analysis may mean assessing a correlation between the first impedance data and second impedance data, and cancelling the alert if the correlation is high. This analysis may indicate that the at-issue lead is measuring impedance consistently with another lead.

In some embodiments, if the second set of information includes impedance measured using electrodes on a lead other than the at-issue lead, analysis may mean assessing variability of between impedance measurements as constrained by second impedance measurements, and cancelling the initial alert if the variability is very low. This analysis, likewise, may indicate that the at-issue lead is measuring impedance consistently with another lead.

In some embodiments, if analysis determines that lead failure alerts are repeatedly being initiated and canceled, criteria for initiating alerts may be modified. For example, impedance thresholds may be increased such that fewer false alerts are initiated. According to embodiments, the analysis may be used to identify situations in which lead failure or other issues tend to occur. That information may be used to adjust monitoring, encourage changes in patient behavior, and/or the like. For example, the analysis may be used to determine that potential lead failure, repositioning, or other issues may be more likely to occur when the subject is in a particular position, when the subject is changing postures, when the subject is engaging in activity at a certain level, at a certain time of day, in response to changes in diet and/or medication, and/or the like.

Additionally, in embodiments, the analysis may be used to rule out lead-related issues such as fracture, dislodgement, perforation, repositioning, and/or the like. That is, for example, while the first set of information may be indicative of a potential lead failure, it may also be indicative of some other event such as, for example, a physiological event. The analysis may be used to rule out the potential lead failure, which may facilitate confirming the physiological event.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for monitoring lead integrity, comprising:
   an implantable medical device (IMD) configured to be implanted within a patient's body, the IMD comprising:
      a housing enclosing a control circuit; and
      a lead, having a first sensor, wherein the lead is coupled to the housing and electrically coupled to the control circuit; and
   at least one processing device configured to:
      identify a first lead failure alert, the first lead failure alert comprising an indication of a potential lead failure based on a first set of information satisfying an alert criterion;
      obtain a second set of information generated by a second sensor associated with the patient's body, the second set of information being posture information;
      perform an evaluation of the first set of information in the context of the second set of information, the evaluation comprising comparing a variability of the first set of information at a fixed posture based upon the posture information; and
      cancel the first lead failure alert when the variability of the first set of information at the fixed posture exceeds a pre-specified threshold.

2. The system of claim 1, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

3. The system of claim 2, the first set of information comprising at least one of a first set of impedance data associated with the lead, wherein the at least one processing device is configured to perform the evaluation by:
   determining whether a subset of the first set of impedance data satisfies the alert criterion, wherein the subset of the first set of impedance data corresponds to at least one instance of a fixed value of the second set of information;
   wherein the processing device is configured to confirm the first lead failure alert if the subset of the first set of impedance data satisfies the alert criterion.

4. The system of claim 2, the first set of information comprising at least one of a first set of impedance data associated with the lead, wherein the first lead failure alert is generated in response to a determination that a first variability exceeds a variability threshold, the first variability comprising a variability of the first set of impedance data, wherein the at least one processing device is configured to perform the evaluation by:
   determining a second variability, the second variability comprising a variability of a subset of the first set of impedance data, wherein the subset of the first set of impedance data corresponds to a plurality of instances of a fixed value of the second set of information; and determining a difference between the first variability and the second variability, wherein the processing device is configured to cancel the first lead failure alert if the difference exceeds a difference threshold.

5. The system of claim 2, the first set of information comprising at least one of a first set of impedance data associated with the lead, wherein the at least one processing device is configured to perform the evaluation by:

determining a variability of a subset of the first set of impedance data, wherein the subset of the first set of impedance data corresponds to a first extreme value of the second set of information and a second extreme value of the second set of information;

wherein the processing device is configured to confirm the first lead failure alert if the variability exceeds a variability threshold.

6. The system of claim 2, the first set of information comprising at least one of a first set of impedance data associated with the lead, wherein the first set of impedance data is obtained using a first sampling frequency, and wherein, in response to receiving the first lead failure alert, the at least one processing device is configured to obtain a second set of impedance data using a second sampling frequency, wherein the second sampling frequency is higher than the first sampling frequency.

7. The system of claim 2, wherein the second set of information further comprises at least one of respiratory data, cardiac cycle data, lead strain data, arm displacement data, and a second set of impedance data, wherein the second set of impedance data is associated with an additional lead.

8. The system of claim 2, wherein the at least one processing device is configured to confirm the first lead failure alert by generating a second lead failure alert, the second lead failure alert comprising an instruction configured to cause a display device to present an indication of failure of the lead.

9. The system of claim 2, wherein the at least one processing device is configured to:

determine a number of first lead failure alerts received within a specified time period;

determine a number of the first lead failure alerts received within the specified time period that were canceled;

determine that the number of the first lead failure alerts received within the specified time period that were canceled exceeds an alert threshold; and adjust the alert criterion in response to determining that the number of the first lead failure alerts received within the specified time period that were canceled exceeds the alert threshold.

10. A system for monitoring lead integrity, comprising:

an implantable medical device (IMD) configured to be implanted within a patient's body, the IMD comprising:
a housing enclosing a control circuit;
a lead, having a first sensor, wherein the lead is coupled to the housing and electrically coupled to the control circuit, wherein the control circuit is configured to obtain a first set of impedance data associated with the lead; and
a first communication component configured to transmit the first set of impedance data; and an external monitoring device (EMD) configured to be disposed outside of the patient's body, the EMD comprising:
a second communication component configured to receive, from the first communication component, the first set of impedance data; and
a processing device configured to (1) identify a first lead failure alert, the first lead failure alert comprising an indication of a potential lead failure based on a first set of information satisfying an alert criterion, the first set of information comprising the first set of impedance data associated with the lead; (2) obtain a second set of information generated by a second sensor associated with patient's body, the second set of information being posture information; (3) perform an evaluation of the first set of information in the context of the second set of information, the evaluation comprising comparing a variability of the first set of information at a fixed posture based upon the posture information; and (4) cancel the first lead failure alert when the variability of the first set of information at the fixed posture exceeds a pre-specified threshold.

11. The system of claim 10, wherein the second sensor comprises at least one of an accelerometer, a sensor disposed on an additional lead coupled to the housing, a displacement sensor configured to detect arm movement, a strain sensor configured to detect tension in the lead, a respiration sensor, and a heart rate sensor.

12. A method of monitoring a status of a lead of an implantable medical device (IMD), the method comprising:

identifying a first lead failure alert, the first lead failure alert comprising an indication of a potential lead failure based on a first set of information satisfying an alert criterion;

obtaining a second set of information generated by a second sensor associated with a patient's body, the second set of information being posture information;

performing an evaluation of the first set of information in the context of the second set of information, the evaluation comprising comparing a variability of the first set of information at a fixed posture based upon the posture information; and canceling the first lead failure alert when the variability of the first set of information at the fixed posture exceeds a pre-specified threshold.

13. The method of claim 12, the first set of information comprising at least one of a first set of impedance data associated with the lead, a set of user input associated with the lead, a set of sensed noise information, a set of pace capture information, a set of sensed intrinsic information, a set of non-sustained tachycardia episode information, and a set of phrenic nerve stimulation information.

14. The method of claim 13, the first set of information comprising at least one of a first set of impedance data associated with the lead, wherein performing the evaluation comprises:

determining whether a subset of the first set of impedance data satisfies the alert criterion, wherein the subset of the first set of impedance data corresponds to at least one instance of a fixed value of the second set of information; and confirming the first lead failure alert if the subset of the first set of impedance data satisfies the alert criterion.

15. The method of claim 13, the first set of information comprising at least one of a first set of impedance data associated with the lead, wherein the second set of information further comprises at least one of respiratory data, cardiac cycle data, strain data, displacement data, and a second set of impedance data, wherein the second set of impedance data is associated with an additional lead.

16. The method of claim 13, wherein the first set of impedance data is obtained using a first sampling frequency, the method further comprising obtaining, in response to receiving the first lead failure alert, the second set of information using a second sampling frequency, wherein the second sampling frequency is higher than the first sampling frequency.

17. The method of claim 13, wherein confirming the first lead failure alert comprises generating a second lead failure alert, the second lead failure alert comprising an instruction configured to cause a display device to present an indication of failure of the lead.

18. The method of claim 13, further comprising:
   determining a number of first lead failure alerts received within a specified time period;
   determining a number of the first lead failure alerts received within the specified time period that were canceled;
   determining that the number of the first lead failure alerts received within the specified time period that were canceled exceeds an alert threshold; and
   adjusting the alert criterion in response to determining that the number of the first lead failure alerts received within the specified time period that were canceled exceeds the alert threshold.

* * * * *